United States Patent [19]

Tanabe

[11] 4,075,413

[45] Feb. 21, 1978

[54] PROCESS FOR PREPARATION OF DIACETOXYBUTENE

[75] Inventor: Yasuo Tanabe, Kurashiki, Japan

[73] Assignee: Mitsubishi Chemical Industries Limited, Tokyo, Japan

[21] Appl. No.: 694,534

[22] Filed: June 10, 1976

[30] Foreign Application Priority Data

June 17, 1975 Japan .................................. 50-73566
Oct. 23, 1975 Japan .............................. 50-127776

[51] Int. Cl.$^2$ ............................................. C07C 67/05
[52] U.S. Cl. .................................................... 560/244
[58] Field of Search ................... 260/497 A; 560/244

[56] References Cited

U.S. PATENT DOCUMENTS

| 3,262,969 | 7/1966 | Clark | 260/497 A |
| 3,671,577 | 6/1972 | Ono | 260/497 A |
| 3,755,423 | 8/1973 | Onoda | 260/497 A |
| 3,872,163 | 3/1975 | Shimizu | 260/497 A |
| 3,922,300 | 11/1975 | Onoda | 260/497 A |

OTHER PUBLICATIONS

Dauphin, Chem. Abst. 67:33006t, (1967).
Jordon, Chem. Abst. 76:14187v, (1972).
Martynova, Chem. Abst. 73:88222g (1970).

Primary Examiner—James O. Thomas, Jr.
Attorney, Agent, or Firm—Bierman and Bierman

[57] ABSTRACT

Diacetoxybutene is prepared by a catalyst reaction of butadiene, acetic acid and oxygen or an oxygen containing gas in the presence of a supported palladium catalyst.

In said reaction, the use of butadiene containing vinylcyclohexene in an amount of not more than 5,000 parts by weight per million parts by weight of butadiene and at least one polymerization inhibitor prevents the lowering of the activity of the catalyst thereby prolonging its useful life.

7 Claims, 5 Drawing Figures

Vinylcyclohexene (ppm)

Elemental Sulfur (ppm)

PROCESS FOR PREPARATION OF DIACETOXYBUTENE

This application claims the priority of Japanese applications Nos. 73,566/1975 and 127,776/1975 filed June 17th, 1975, and Oct. 23rd, 1975, respectively.

BACKGROUND OF THE INVENTION

1. Field of the Invention

This invention relates to an improvement in the process of preparing diacetoxybutene by a catalytic reaction of butadiene, acetic acid and oxygen or an oxygen-containing gas in the presence of a palladium catalyst.

2. Description of the Prior Art

It is known that diacetoxybutene may be produced by reacting butadiene, acetic acid and oxygen in the presence of a palladium catalyst, and various methods have been proposed for this reaction. However, it has been found that when the reaction runs for a substantial length of time, a sharp drop in the catalytic activity occurs, thereby making it impossible to maintain an industrially satisfactory reaction rate for a long period of time.

SUMMARY OF THE INVENTION

Accordingly, it is one object of this invention to provide an industrially advantageous process for manufacturing diacetoxybutene.

It is another object of this invention to prevent the lowering of the catalytic activity and to prolong the useful life of the catalyst, so that the acetoxylation reaction may be carried out for long periods of time.

Still another object of this invention is to provide a process for producing diacetoxybutene in high yields.

Briefly, these and other objects will hereinafter become more readily apparent, have been attained by reacting butadiene, acetic acid and molecular oxygen in the presence of a supported palladium catalyst.

DETAILED DESCRIPTION OF THE PREFERRED EMBODIMENTS

Figure 1:
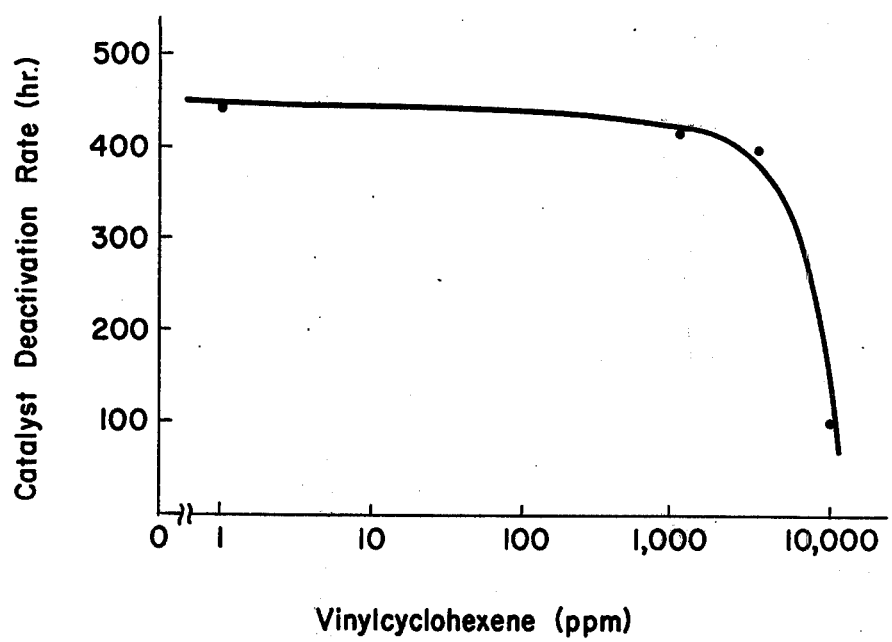
FIG. 1 is a graph illustrating the influence that the amount of vinylcyclohexene has upon the catalyst activity in the acetoxylation reaction.

The supported palladium catalysts preferably used in the reaction of the present invention are the ones in which a palladium metal alone or a palladium metal and at least one co-catalyst metal selected from bismuth, selenium, antimony and tellurium are supported on a carrier. Any suitable type of catalyst carrier may be used in this invention including active carbon, silica gel, silica-alumina, alumina, clay, bauxite, magnesia, diatomaceous earth and pumice. The amount of palladium metal and the co-catalyst metal carried in the catalyst is usually within the range of 0.1 to 20% (by weight) of the total amount of catalyst in the case of palladium metal, and within the range of 0.01 to 30% (by weight) of the total amount of catalyst in the case of a co-catalyst metal. Instead of supporting the co-catalyst component on the carrier, it is possible to mix a co-catalyst such as an antimony, selenium, tellurium or bismuth compound in the reaction solution, and, if need be, halogen ions may also be introduced into the reaction solution. The reaction is usually carried out within a temperature range of 50° to 160° C, preferably 80° to 120° C. In determining the pressure at which the reaction will be run, the partial pressure of oxygen and the explosive nature of a mixture of butadiene and oxygen must be considered. The pressure used is higher than normal and is usually from 5 to 300 kg/cm$^2$G, preferably 40 to 120 kg/cm$^2$G. The reaction may be carried out in many different ways. Examples are a fixed-bed reaction wherein the catalyst is fixed in a reactor, or a suspension reaction wherein the catalyst particles are suspended in the reactant. The former is more advantageous in industrial applications.

Any suitable method may be employed for contacting the reaction material with the catalyst as long as sufficient contact can be achieved. It is possible to employ a gas (such as oxygen-containing gas) and liquid (such as acetic acid and butadiene) parallel flow system or a gas and liquid counter-current system. The most advantageous system to use is an "irrigated packed-bed system" which is a type of fixed-bed process in which the liquid material flows downwardly over the fixed catalyst bed while the gaseous material also travels downwardly.

The ratio of acetic acid to butadiene in the reaction material may be varied, but usually acetic acid is used in an amount of 1 to 10 parts by weight (preferably 4 to 6 parts by weight) per part by weight of butadiene. The oxygen-containing gas is used in an amount of 5 to 20 moles, preferably 8 to 15 moles, per mole of acetic acid.

The reactor used in the present invention may be a multi-tubular external cooling type, adiabatic multi-stage inter-cooling type or any other suitable type, provided that the temperature of the reaction can be easily controlled. The reactor should be constructed from steel having a Ni, Cr, and Mo content at least equal to those of SUS 316 (Japanese Industrial Standards).

According to the present invention, the amount of vinylcyclohexene contained in the butadiene must be kept below a fixed level and the butadiene must be reacted in the presence of a polymerization inhibitor.

A small amount of impurities such as carbonyl compounds, acetylenes, etc., are contained in industrial grade butadiene. Among such impurities, vinylcyclohexene, if contained in excess, may give rise to a side reaction and cause excessive deactivation of the acetoxylation reaction catalyst. As a result of the polymerization process, butadiene, by itself or in combination with the reaction product, deposits and forms an inactive film on the surface of the catalyst. This effect is illustrated by the graph of FIG. 1 which shows the relationship between the amount of vinylcyclohexene found in the reaction system and the catalyst deactivation rate. The ordinate indicates the catalyst deactivation rate (time taken until the initial catalyst activity is reduced by half) and the abscissa indicates the parts by weight of vinylcyclohexene per million parts by weight of butadiene. The graph of FIG. 1 is based on the data obtained by reacting 40 g/hr of acetic acid, 15 g/hr of butadiene and 160 Nl/hr of a gaseous mixture of nitrogen and oxygen. 20 gr of an acetoxylation catalyst are used and reaction conditions are under 40 kg/cm$^2$ gauge pressure, 100° C temperature and a 3% oxygen concentration.

The influence of vinylcyclohexene upon the activity of the catalyst was tested by introducing various amounts of vinylcyclohexene to the butadiene reaction. The catalyst used was one in which Pd (2 wt %) and Te (Te/Pd = 0.30 by atomic ratio) were carried on 4- to 6-mesh active carbon (surface area 600 m$^2$/g). As is apparent from the results obtained, the activity of the catalyst shows a sharp drop if the amount of vinylcyclohexene exceeds 5000 parts by weight per million parts by weight of butadiene (ppm). Thus, it is noted that the amount of vinylcyclohexene to be added to the reaction system should be not more than 5000 ppm preferably 1000 to 50 ppm.

If the concentration of vinylcyclohexene present is greater than the aforementioned range, it should be removed by a convenient method such as distillation or adsorption. Since vinylcyclohexene could be also formed during the storage of butadiene, it is advantageous to have at least one polymerization inhibitor contained in butadiene.

Various types of polymerization inhibitors for unsaturated compounds are known, and many of them can be used in the present invention, including phenols and quinone and derivatives thereof, such as hydroquinone; 2,5-di-t-butylhydroquinone; 2,5-di-t-amylhydroquinone; t-butylcatechol; 2,6- or 2,4-di-t-butylphenol; 2,4-di-t-butyl-p- cresol (BHT); 4,4'-butylidene bis (3-methyl-6-t-butylphenol); 2,2'-methylene bis (4-methyl-6-t-butylphenol); quinone; anthraquinone; elemental sulfur; etc., The amount of the polymerization inhibitor to be used in the reaction may be varied according to the nature of the inhibitor selected.

When a polymerization inhibitor other than elemental sulfur is used, an amount less than 2 parts by weight per million parts by weight of butadiene (ppm) produces no significant effect, while an amount greater than 200 ppm may give rise to various undesirable side reactions. Therefore, polymerization inhibitors are usually used in an amount of 2 to 200 ppm and preferably 5 to 50 ppm.

When elemental sulfur is used, it is added within the range of 10 to 7000 parts by weight, most preferably 200 to 2000 parts by weight, per million parts by weight of butadiene. When 200 to 2000 ppm of elemental sulfur is used, the useful life of the catalyst is more than doubled.

Figure 2:
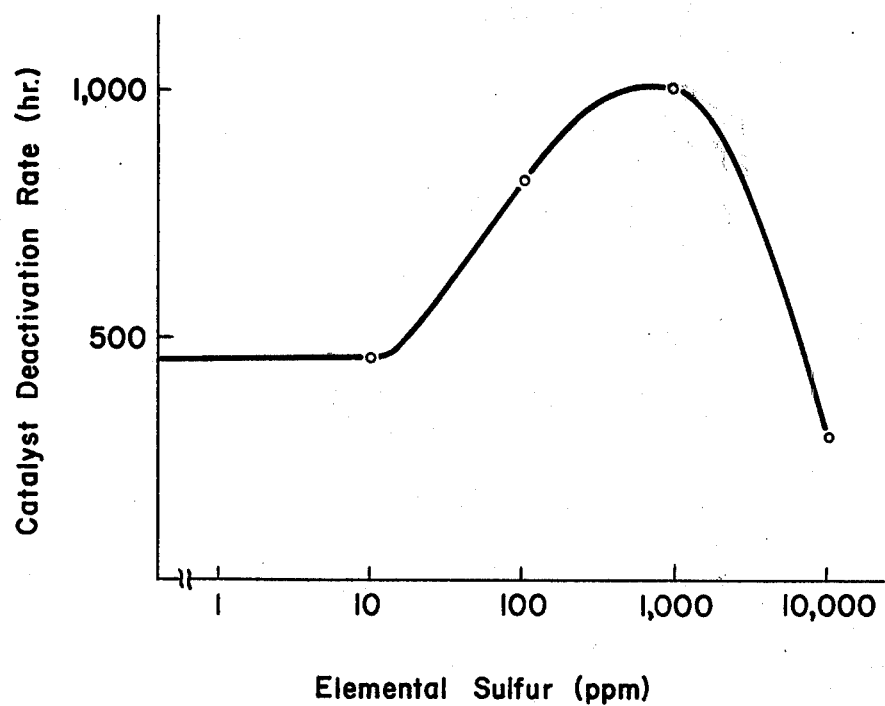
FIG. 2 is a graph showing the effect that the amount of elemental sulfur has upon the catalyst activity in the acetoxylation reaction.

Referring to the drawings, FIG. 2 shows the relationship between the amount of elemental sulfur added to the reaction system and the deactivation rate of the catalyst. The ordinate expresses the catalyst deactivation rate (time required for the initial activity to be reduced by half) and the abscissa expresses the amount of elemental sulfur used, based on the parts by weight of butadiene. The graph of FIG. 2 is based on the results obtained from the investigation of the effect that elemental sulfur has upon the activity of the catalyst. Various amounts of elemental sulfur are added along with butadiene to the reaction system. The reaction is carried out using 40 g/hr of acetic acid, 15 g/hr of butadiene and 160 Nl/hr of a nitrogen-oxygen gas mixture in the presence of 20 gr of a palladium catalyst and at temperature of 100° C and under a pressure of 40 kg/cm$^2$ gauge, with the oxygen concentration being adjusted to 3%. 20 gr. of a catalyst were used and it was prepared by supporting Pd (2 % by weight) and Te (Te/Pd = 0.30 by atomic ratio) on 4- to 6-mesh active carbon (surface area 850 m$^2$/g). It is apparent from these results that, if too little elemental sulfur is added, it will produce no significant effect, while if too much sulfur is added, it will prove to be detrimental to the activity of the catalyst.

Figure 3:
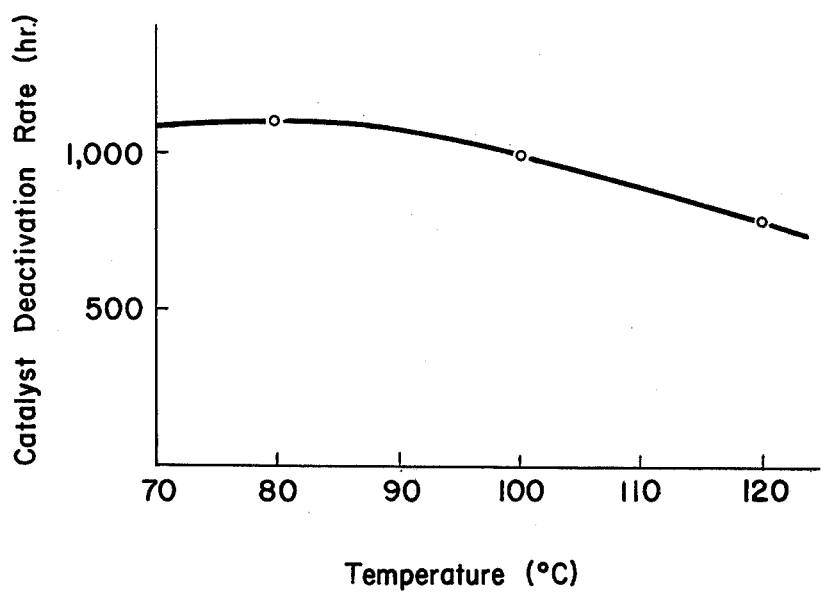
FIG. 3 is a graph showing the effect of temperature on the catalyst activity in the acetoxylation reaction when elemental sulfur was added in an amount of 1000 ppm (by weight).

FIG. 3 shows the relationship between the reaction temperature and the catalyst deactivation rate (the time required for the initial activity to be reduced by half) when elemental sulfur was added in an amount of 1000 ppm. The ordinate expresses the catalyst deactivation rate the abscissa expresses the reaction temperature. The graph of FIG. 3 is based on the results of the reaction which was run under the same conditions as used in FIG. 2 except for a change in the reaction temperature. When the reaction temperature is lower than 80° C, the polymerization rate of butadiene and the reaction product is not high enough to appreciably influence the activity of the catalyst. On the other hand, when the reaction temperature exceeds 80° C, the polymerization rate is elevated resulting in a sharp drop in the activity of the catalyst. However, as is apparent from FIG. 3, if elemental sulfur is introduced according to the method of this invention, the drop in the activity of the catalyst is very effectively arrested even at temperatures exceeding 80° C.

Figure 4:
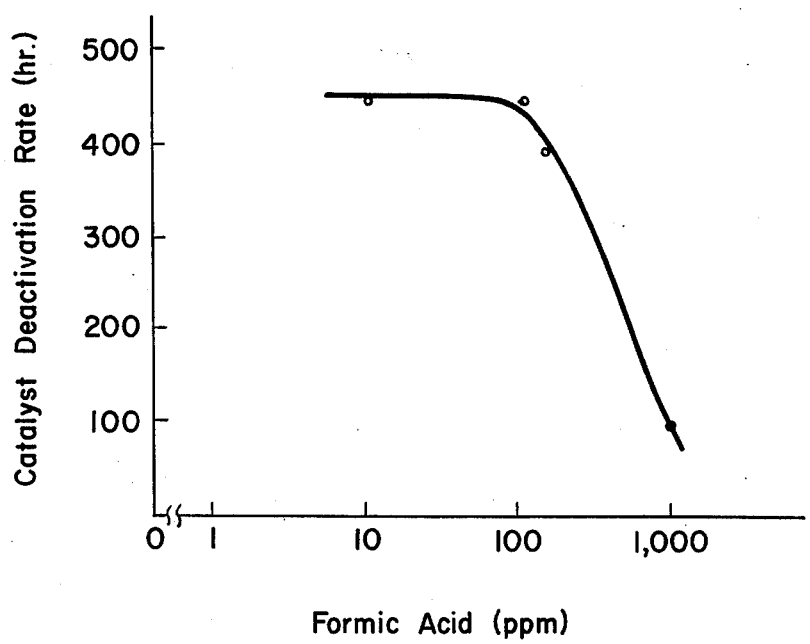
FIG. 4 is a graph illustrating the influence that the amount of formic acid has upon the catalyst activity in the acetoxylation reaction.

Formic acid is usually present in industrial grade acetic acid (which is another material used in the acetoxylation reaction) and the amount of formic acid present also affects the activity of the acetoxylation reaction catalyst. Thus, as noted in the graph of FIG. 4, although the reaction is not adversely effected if the amount of formic acid present is less than 100 parts by weight per million parts by weight of acetic acid (ppm), a sharp drop in the activity of the catalyst is caused if the concentration is greater than 100 ppm, particularly if it is in excess of 200 ppm. The graph of FIG. 4 is based on data obtained by reacting 40 g/hr of acetic acid, 15 g/hr of butadiene and 160 Nl/hr of a gaseous mixture of nitrogen and oxygen in the presence of 20 gr of an acetoxylation catalyst under a pressure of 40 kg/cm$^2$G, at temperature of 100° C and with an oxygen concentration of 3%.

The influence of formic acid upon the activity of the catalyst was examined by varying the formic acid content of the acetic acid. The ordinate indicates the catalyst deactivation rate (the time required for the initial catalyst activity to drop to one-half its initial value) and the abscissa indicates the parts by weight of formic acid per million parts by weight of acetic acid. As is apparent from these results, the amount of formic acid in the reaction should not be more than 200 parts by weight per million parts by weight of acetic acid. If the formic acid content is greater than 200 parts, the excess portion is removed by distillation or by contacting it with a catalyst (such as palladium) at about 80° C prior to introducing it into the reaction system. It was found that more than 20% (by weight) of the formic acid is decomposed in one pass of the acetoxylation reaction. This means that no serious accumulation of formic acid occurs even if acetic acid is used cyclically in the reaction system.

In introducing the polymerization inhibitors into the reaction system, no specific restriction is imposed. It may, for example, be contained in the starting material such as butadiene or acetic acid. As for elemental sulfur, before it is placed in the reactor, it may be dissolved in liquid butadiene or acetic acid or a mixture thereof. It is desirable to add the required amount of elemental sulfur dissolved in acetic acid to the reaction zone by means of a pump. In this case, it is preferred to add the sulfur dissolved in acetic acid prior to the introduction of butadiene to the preheater where the liquid butadiene is exposed to a temperature higher than 80° C.

Although the preheating of butadiene may be accomplished by treating butadiene alone, it is more advantageous to preheat a mixture of butadiene and acetic acid and/or other oxygen-containing gas.

The elemental sulfur supplied to the reaction system may not necessarily be fresh; the same is true of the sulfur obtained by recycling the reaction solution. The recycled reaction solution is capable of preventing the generation of polymers. The drawback of using a recycled solution is that the reaction rate is retarded by the reaction product. The use of the recycled solution adds an additional amount of reaction product to that formed during the reaction.

As a result of a study of the effective utilization of elemental sulfur in the reaction system, the present inventor has found that the acetoxylation reaction will not be affected if the residue of the reaction product from which the desired diacetoxybutene has been distilled is added to the reaction system without altering it. The addition of said residue will satisfactorily control the polymerization reaction caused by elemental sulfur.

According to the method of this invention, diacetoxybutene is distilled from the actoxylation reaction product which contains elemental sulfur, and at least a part of the obtained residue is circulated back into the reaction system to be used as the elemental sulfur source. Although various methods may be employed in this process, it is preferred to employ a method in which butadiene, and then the non-reacted acetic acid and finally the end product, diacetoxybutene, are distilled from the reaction product, and the residue is recycled to the reaction system.

Figure 5:
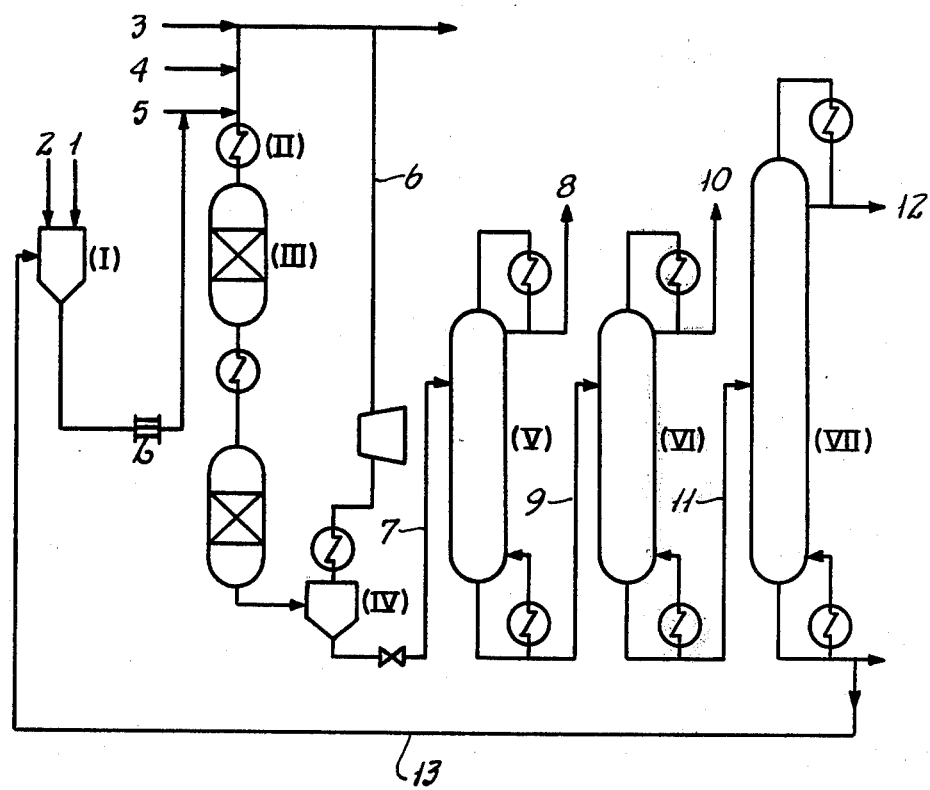
FIG. 5 is a flow sheet illustrating an embodiment of the present invention, where (I) designates a dissolving tank, (II) a preheater, (III) a reactor, (IV) a gas-liquid separator, and (V), (VI) and (VII) distillation columns.

A typical example of the recycling method used in the present invention is described with reference to FIG. 5.

Elemental sulfur and acetic acid are supplied from conduits 1 and 2 into a dissolving tank (I) and dissolved therein. Oxygen or an oxygen-containing gas and butadiene are supplied from conduits 3 and 4 into a preheater (II). The preheater is also fed from conduit 5, with acetic acid and sulfur which is conducted from the dissolving tank (I). The mixture is heated therein to a predetermined temperature, and then introduced into two sets of acetoxylation reaction towers (III). The reaction product is led into a gas-liquid separator (IV) where said product is separated into a gaseous portion and a liquid portion, the former being cooled and compressed, with a part thereof being circulated back into the reaction system through a conduit 6, while the remainder is discharged. The liquid portion is guided into a butadiene recovery tower (V) through a pipe 7, and butadiene is distilled and recovered from 8 while the liquid at the bottom of the tower is conducted into acetic acid recovery tower (VI) through pipe 9. The fraction composed mainly of acetic acid is removed from 10 and the liquid at the bottom of the tower is guided into an acetoxybutene separator (VII) through a conduit II. Diacetoxybutene is removed through pipe 12 and the residue withdrawn from the bottom of the tower is fed back into the dissolving tank (I) and again supplied into the reaction system.

The rate of recycling residue cannot be determined definitively as it differs depending on the reaction conditions, concentration conditions in the distillation process, and the amount of fresh elemental sulfur. Usually it is 5 to 80% by weight, preferably 10 to 50% by weight, of the total amount of residue found at the bottom of the diactoxybutene separation tower.

According to the method of the present invention, the lowering of the activity of the catalyst can be prevented, thereby increasing its useful life and lengthening the amount of time the acetoxylation reaction may be run. This is accomplished by lowering to a specified level the amount of poisonous material contained in the butadiene and acetic acid supplied to the reaction and by adding a polymerization inhibitor. The use of a polymerization inhibitor not only prevents the formation of vinylcyclohexene, but also prevents the polymerization of butadiene. Additionally, when elemental sulfur is used as an inhibitor, the residue formed as a result of the distillation of diacetoxybutene is recycled into the reaction zone to be used as a source of elemental sulfur. Accordingly, the method of the present invention allows the economical production of diacetoxybutene in a process that has broad industrial applications.

Having generally described the invention, a more complete understanding can be obtained by reference to specific examples which are included for the purpose of illustration only and are not intended to limit the scope of the invention.

EXAMPLE 1

Catalyst 10 mg-mol of palladium chloride and 10 mg-mol of tellurium dioxide were dissolved in 80 ml of 6N-hydrochloric acid; and, after adding thereto 20 g of 4- and 6-mesh active carbon, the mixture was slowly dried and solidified over a water bath. Then the mixture was subjected to a nitrogen stream at 150° C for 2 hours in order to further dry the mixture. At a flow rate of 1 liter/min, it was further subjected to treatment with nitrogen which had been previously saturated with water and methanol at room temperature. In order to effect reduction, this was done at 200° C for 2 hours and then at 400° C for 1 hour, thereby resulting in a useable catalyst.

Acetoxylation Reaction

The thus prepared catalyst was charged into a jacketed reactor made from SUS 316L with an inner diameter of 20 mm and a length of 300 mm, the reactor temperature being maintained at 100° C. Then, 40 g/hr of acetic acid (containing 10 ppm of formic acid), 15 g/hr of butadiene (containing 20 ppm of p-t-butylcatechol and 1 ppm of vinylcyclohexene) and 160 Nl/hr of an oxygen-containing gas ($O_2$ content in $N_2$ being 3%) were placed into the top of the reactor under a pressure of 40 kg/cm$^2$ gauge. The reaction solution which was withdrawn from the bottom of the reactor was cooled to 20° C, and after eliminating the dissolved butadiene, it was analyzed by gas chromatography. The result showed a 16% (by weight) concentration of 1,4-diacetoxybutene-2 in the reaction solution. After the reaction was continued under these conditions for 450 hours, the concentration of 1,4-diacetoxybutene-2 in the produced reaction solution dropped to 8% (by weight).

EXAMPLE 2

Reactions were carried out under the same conditions as in Example 1 except for a change in the concentration of vinyl-cyclohexene contained in the butadiene as shown in the following table. The time required for the concentration of 1,4-diacetoxybutene-2 in the reaction solution to be reduced to 8% (by weight) was measured. The results are shown in the following table.

| Case | Vinylcyclohexene content (ppm) | Time (hr) |
| --- | --- | --- |
| 1 | 10 | 450 |
| 2 | 1,000 | 425 |
| 3 | 5,000 | 400 |
| Comparative Case | 10,000 | 100 |

EXAMPLE 3

The reaction was carried out under the same conditions as in Example 1 except for the addition of elemental sulfur dissolved in acetic acid (containing 10 ppm of formic acid) and for a change in the amount of elemental sulfur used based upon the butadiene concentration as shown in the following table. The time required for the concentration of 1,4-diacetoxybutene in the produced reaction solution to be reduced to 8% (by weight) was measured. The results are shown below.

| Case | Sulfur (ppm) | Time (hr) |
| --- | --- | --- |
| 1 | 10 | 450 |
| 2 | 100 | 800 |
| 3 | 1,000 | 1,000 |
| 4 | 5,000 | 600 |
| 5 | 10,000 | 300 |

EXAMPLE 4

After separating butadiene from the reaction product obtained in Case 3 of Example 3, 40 kg of the reaction product was fed into the bottom of a batch distillation column made from SUS 316 L with inner diameter of 50 mm and a height of 3 m (packed with SUS 316 L Dixon packing). First, acetic acid was fractionated under a pressure of 150 mmHg, and then diacetoxybutene was fractionated under a pressure of 50 mmHg to obtain 500 g of residue.

The entire amount of this residue was dissolved in 40 kg of fresh acetic acid, and by using this in place of the acetic acid used in Example 1, the process of Example 1 was repeated. It was discovered that 700 hours were passed before the concentration of 1,4-diacetoxybutene in the end product was reduced by fifty percent.

EXAMPLE 5

Reactions were carried out by following the same process as Example 1 except that the vinylcyclohexene content of butadiene was increased to 10 ppm and formic acid content of the acetic acid was varied as shown in the following table. The time required for the concentration of 1,4-diacetoxybutene-2 in the produced reaction solution to drop to 8% (by weight) was measured. The results are shown in the following table.

| Case | Formic acid content (ppm) | Time (hr) |
| --- | --- | --- |
| 1 | 100 | 450 |
| 2 | 200 | 400 |
| Comparative Case | 1,000 | 100 |

EXAMPLE 6

A reaction was conducted under the same conditions as in Example 1 except that butadiene containing 10 ppm of vincylcyclohexene was used and the feed rate of acetic acid was doubled. It was discovered that the initial concentration (8% by weight) of 1,4-diacetoxybutene-2 in the produced reaction solution dropped to 4% (by weight) after 450 hours.

EXAMPLE 7

The process of Example 1 was repeated except that butadiene containing 1000 ppm of vinylcyclohexene was used and the feed rate was doubled. As a result, the initial concentration (16% by weight) of 1,4-diacetoxybutene in the produced reaction solution dropped to 8% (by weight) in 425 hours.

EXAMPLE 8

4 kg of the reaction solution obtained in Case 1 of Example 5 was distilled to obtain 3.8 kg of an acetic acid fraction, and to it was added 0.8 kg of fresh acetic acid (containing 70 ppm of formic acid). After adjusting the formic acid concentration to 100 ppm, the mixture was subjected to a reaction in the same manner as used in Case 1 of Example 5, obtaining substantially the same results.

EXAMPLE 9

4 kg of the reaction solution obtained in Case 2 of Example 2 was distilled to obtain an acetic acid fraction (containing 10 ppm of vinylcyclohexene), and 0.9 kg of freshly acetic acid was added to 3.1 kg of said acetic acid fraction to adjust the vinylcyclohexene concentration to 1000 ppm. In the meantime, butadiene was prepared containing 10 ppm of vinylcyclohexene and 20 ppm of p-t-butyl-catechol. Both solutions were reacted under the same conditions as used in Case 2 of Example 2, obtaining substantially the same results.

Having now fully described the invention, it will be apparent to one of ordinary skill in the art that many changes, and modifications can be made thereto without departing from the spirit or scope of the invention as set forth herein.

What is claimed as new and intended to be covered by Letters Patent is:

1. In a process for the preparation of diacetoxybutene by a catalytic reaction of butadiene, acetic acid and oxygen or an oxygen-containing gas in the presence of a catalyst containing palladium metal on a support, the improvement which comprises carrying out the reaction by using butadiene containing vinylcyclohexene in an amount of 1 to 5,000 parts by weight per million parts by weight of butadiene and at least one polymerization inhibitor selected from the group consisting of quinone, hydroquinone, 2,5-di-t-butyl-hydroquinone, 2,5-di-t-amylhydroquinone, anthraquinone, phenol, t-butylcatechol, 2,6-di-t-butylphenol, 2,4-di-t-butylphenol, 2,4-di-t-butyl-p-cresol, 4,4'-butylidene-bis (3-methyl-6-t-butylphenol), 2,2-methylene-bis (4-methyl-6-t-butylphenol), and elemental sulfur, the amount of the polymerization inhibitor other than elemental sulfur being from 5 to 50 parts by weight per million parts by weight of butadiene and the amount of elemental sulfur being from 10 to 7,000 parts by weight per million parts by weight of said butadiene.

2. The process according to claim 1 in which the vinylcyclohexene content of said butadiene is from 50 to 1,000 parts by weight per million parts by weight of said butadiene.

3. The process according to claim 1 in which the amount of elemental sulfur is from 200 to 2,000 parts by weight per million parts by weight of butadiene.

4. The process according to claim 1 in which acetic acid contains formic acid in an amount of 10 to 200 parts by weight per million parts by weight of said acetic acid.

5. In a process for the preparation of diacetoxybutene by a catalytic reaction of butadiene, acetic acid and oxygen or an oxygen-containing gas in the presence of a catalyst containing palladium metal on a support, the improvement comprising carrying out the reaction by using butadiene containing vinylcyclohexene in an amount of 1 to 5,000 parts by weight per million parts by weight of said butadiene in the presence of elemental sulfur in an amount of 10 to 7,000 parts by weight per million parts by weight of said butadiene, to thereby form a reaction product, successively distilling butadiene, acetic acid and diacetoxybutene from the reaction product, wherein a residue is formed and recycling the residue to the reaction.

6. The process according to claim 5 further comprising forming a residue and recycling an amount equal to 5 to 80% by weight of said residue to said reaction.

7. The process according to claim 5 wherein the amount recycled is from 10 to 50 percent by weight of the total amount of said residue.

* * * * *